United States Patent [19]

Meyerovich

[11] Patent Number: 5,370,140
[45] Date of Patent: Dec. 6, 1994

[54] SIDE GUARD PROTECTION DEVICE AND METHOD FOR TREATING INGROWN NAILS

[76] Inventor: John Meyerovich, 496 W. Willow Ct., Fox Point, Wis. 53217

[21] Appl. No.: 86,647
[22] Filed: Jul. 2, 1993
[51] Int. Cl.⁵ ............................................. A45D 24/00
[52] U.S. Cl. ...................................... 132/200; 132/73; 602/31
[58] Field of Search ................ 132/73, 73.5, 200, 285; 602/31; 606/1; 128/898

[56] References Cited

U.S. PATENT DOCUMENTS

| | | | |
|---|---|---|---|
| 137,106 | 3/1873 | Stedman . | |
| 1,596,532 | 8/1926 | Haener . | |
| 2,342,530 | 2/1944 | Coates | 128/81 |
| 2,479,514 | 8/1949 | Rucker | 132/75.6 |
| 2,505,086 | 4/1950 | Andrews | 128/81 |
| 2,542,324 | 2/1951 | Gibbons | 602/31 |
| 2,920,621 | 1/1960 | Fettig | 128/81 |
| 3,799,160 | 3/1974 | Hahn | 128/81 |
| 3,981,298 | 9/1976 | Vironda | 128/81 |
| 4,674,486 | 6/1987 | Hoffman | 128/81 |
| 4,936,322 | 6/1990 | DeSantis | 132/75.6 |
| 4,964,213 | 10/1990 | Suggs | 30/28 |
| 5,012,799 | 5/1991 | Remmen | 128/81 |
| 5,197,961 | 3/1993 | Castle | 606/1 |
| 5,226,433 | 7/1993 | Garia-Carreé | 132/73 |

Primary Examiner—Gene Mancene
Assistant Examiner—Frank A. LaViola
Attorney, Agent, or Firm—Nilles & Nilles

[57] ABSTRACT

A side guard protection device and method for treating ingrown nails includes a plastic, flattened U-shaped channel member received down the side edge of the nail. One arm of the guard extends under the ingrown edge of the nail and the other arm of the guard lies across the upper surface of the nail, with the two arms joined at a curved section which fits snugly around the edge of the nail. The side guard is applied to one or both edges of an ingrown nail with the use of an adhesive and catalyst for instantly bonding the guard to the nail, and the adhesive is used to provide a smooth level surface over the top of the nail. The side guard directs the nail to grow straight, and the guard advances with and may be trimmed with the nail as it grows.

4 Claims, 2 Drawing Sheets

SIDE GUARD PROTECTION DEVICE AND METHOD FOR TREATING INGROWN NAILS

BACKGROUND OF THE INVENTION

1. Field of the Invention

This invention relates to a device and method for treating ingrown nails on toes and fingers.

2. Background of the Related Art

A normal nail on a toe or finger has a relatively large radius or curvature corresponding generally to the circumference of the toe or finger. However, certain conditions may cause the edge or edges of the nail to become curved or curled inwardly, especially at or near the end of the nail. As a result, the interned edge or edges of the nail protrude into the flesh of the toe or finger, giving rise to the condition known as ingrown toenail or ingrown finger nail.

Since an ingrown nail may cause discomfort and in some cases severe pain, a number of devices and appliances have been devised to treat the condition. For example, U.S. Pat. No. 137,106 to E. E. Stedman discloses a curved spring which overlies the toe and engages the edges of the nail. U.S. Pat. No. 1,596,532 to F. Haener discloses a double walled guard with portions adapted to lie above and below the nail, respectively, and double walled arms extending rearwardly to embrace the edges of the nail. U.S. Pat. No. 2,342,530 to E. F. Coates discloses a protective nail device which includes two complementary sections, with each section having a thickened edge portion which lies along the edge of the nail and a relatively thin upper portion which lies along the top of the nail, and the device extends forward of the end of the nail to hold the flesh in its proper position with respect to the nail. U.S. Pat. No. 2,505,086 to R. P. Andrews discloses a wide sheet of plastic with an attaching flap which is inserted under the ingrown side of the nail. U.S. Pat. No. 2,920,621 discloses a nylon channel inserted under the edge of the nail to serve as an abutment for a lipped metal strap which lies horizontally across the face of the nail and is then taped into position with adhesive tape. U.S. Pat. No. 3,981,298 to Philip G. Vironda discloses a liquid material spread across the base of the nail, causing the material to harden and to become adhered to the nail and to serve as a support to retain the form of the nail as it grows. U.S. Pat. No. 4,674,486 to Ronald G. Hoffman discloses a resilient strip of material placed on the upper surface of the toenail, which urges the side edges of the nail upwardly and thereby tending to fatten the toenail and eliminated the inwardly curved edges of the ingrown nail. U.S. Pat. No. 5,012,799 to Werner G. Remmen discloses a steel wire spring having a central inverted V-shaped bridge, and the free ends of the wire are curved downwardly to form small lips slipped over the side edges of the toenail.

A number of nail trimming devices and instruments have also been devised for the purpose of cutting and treating ingrown toenails, including U.S. Pat. No. 2,479,514 to L. C. Rucker, U.S. Pat. No. 3,799,160 to Harry L. Hahn, U.S. Pat. No. 4,936,322 to Damian G. DeSantis, and U.S. Pat. No. 4,964,213 to Patricia A. Suggs.

Despite the number of devices and methods which have been developed for the treatment of ingrown nails, none have been fully satisfactory to the podiatry and beauty industries. A significant number of people continue to have discomfort and severe pain as a result of ingrown nails.

SUMMARY OF THE INVENTION

A novel side guard protection device designed specifically for the treatment of ingrown toenails and fingernails, and a method of utilizing the guard in order to treat and inhibit the reoccurrence of ingrown nails, is disclosed.

The guard is manufactured of a suitable plastic and is made available in varying configurations and thicknesses to accommodate varying types and sizes of toes, fingers and nails. The guard comprises a flattened U-shaped nail guard which is received down the side of the nail, with one arm of the U-shaped nail guard extending under the edge of the nail, and the other arm of the U-shaped nail guard lying over the top surface of the nail. The guard is affixed to the nail through the use of an adhesive and catalyst. Adhesive is further applied over the top of the nail to provide a smooth surface and provide a straight top edge for the nail. The guard forces the nail to grow straight. The guard will advance with the nail and may be trimmed as the nail grows.

The invention is not based on any wire clips or metal devices with or without hooks, nor on any unnecessary application of plastic sheets or self-adhesive tapes. The invention can be used by any podiatrist or nail technician.

The primary objects of the invention are therefore to provide a means and method for treating and preventing the reoccurrence of ingrown toenails and ingrown finger nails; to provide a side guard protection device received down the edge of the nail for guiding the nail in a normal straight path as it grows; to provide a nail guard which is easily applied through the use of an adhesive and catalyst; to provide a device which will grow naturally with the nail and guide the nail as it grows; to provide a device which can be trimmed as the nail grows; to provide a device which will have a smooth flat surface over the top of the nail; and, to provide a device which aesthetically appears like a normal nail.

Other objects and advantages of the invention will become apparent from the following description which sets forth, by way of illustration and example, certain preferred embodiments of the invention.

BRIEF DESCRIPTION OF THE DRAWINGS

The drawings, which constitute a part of the specification and include exemplary embodiments of the present invention, include the following.

DETAILED DESCRIPTION

Figure 1:
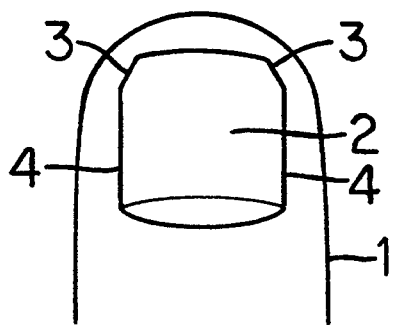
FIGS. 1-8 are top views of a toe or finger showing the steps of the method for treating ingrown nails in accordance with the present invention.
Figure 2:
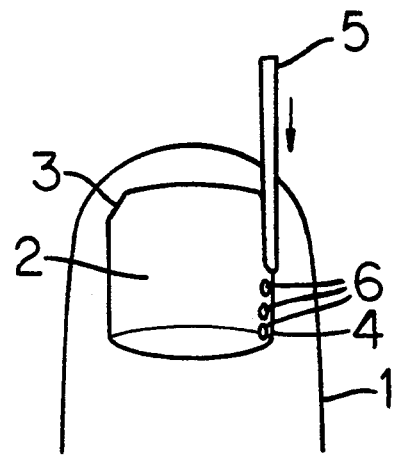
Figure 3:
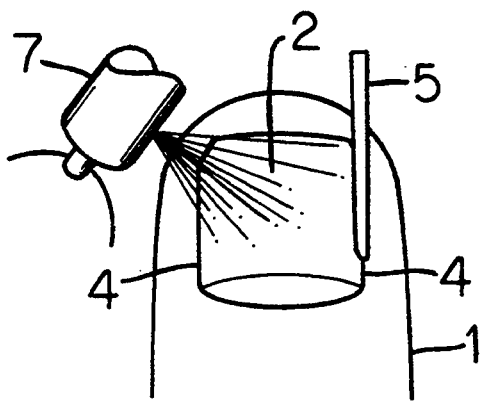
Figure 4:
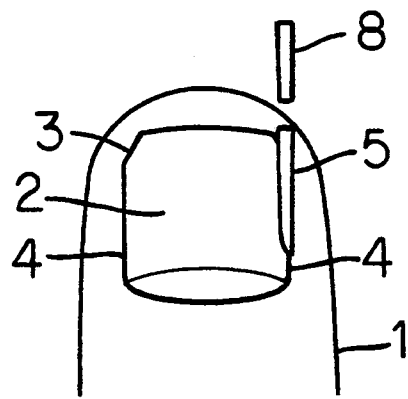
Figure 5:
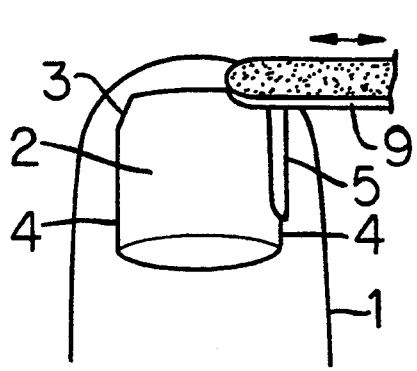
Figure 6:
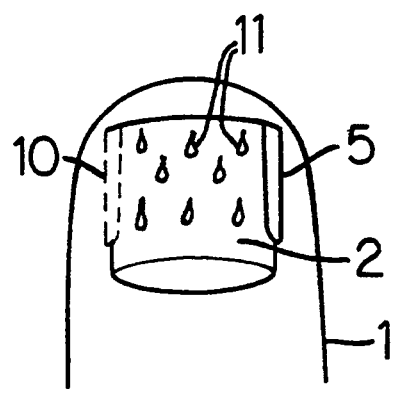
Figure 7:
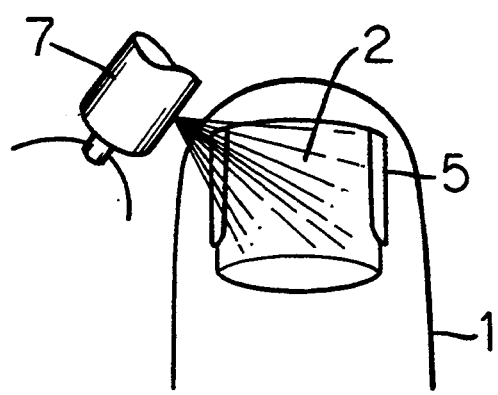
Figure 8:
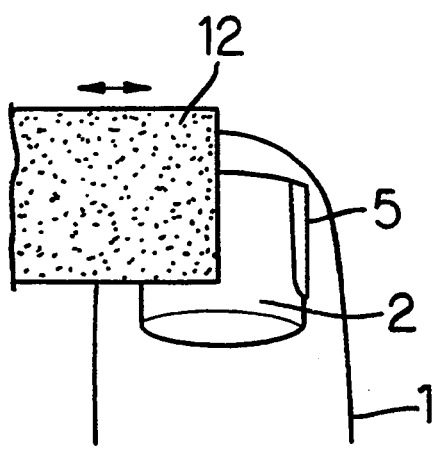

Referring to FIGS. 1-8, on a toe or finger 1, the nail 2 grows from the base outwardly toward the end of the digit 1. A nail 2 usually becomes ingrown along the edge 4, typically near the end of the nail. The ingrown corners 3 of the nail 2 are clipped with a scissors or otherwise removed.

A side guard protection device 5 is applied to the ingrown edge 4 of the nail 2. A small amount of adhesive 6 is applied sparingly to the edge 4 of the nail 2.

Also, a small amount of adhesive 6 may be applied with an orangewood stick or other device to the inside cavity of the side guard protector 5. Adhesive 6 should be applied within the side guard protector 5 for only approximately the length of the nail edge 4 it will be adhered to. The side guard protector 5 is then gently slid under the side edge 4 of the nail 2, beginning at the free end, and continuing toward the nail base as far as comfortably possible.

Once the side guard protector 5 is properly positioned, a catalyst 7 is sprayed onto the adhesive 6 for instantly adhering the guard 5 to the edge 4 of the nail 2. The excess portion 8 of the guard 5 is clipped straight across at the length that would allow the free end of the nail 2 to be shaped square, and the trim piece 8 of the guard may be used on the other side of the nail, if that is also ingrown 3, or it may be discarded.

The free end of the nail is then filed square and straight across 9. It is important that the free end of the nail 2 is not rounded at the corners, but is square and straight. A second guard 10, if necessary, is applied using the same technique described above for the first guard 5.

A leveling layer of adhesive 11 is applied to the top of the nail plate 2 level with the thickness of the nail side guard 5. The adhesive 11 is spread evenly with an orangewood stick or other device over the entire nail surface 2, with the adhesive being kept approximately ⅛ of an inch away from the cuticle area. The catalyst 7 is again sprayed for instantly solidifying the adhesive 11. The surface and free end of the nail 2 is then buffed to a smooth finish.

Figure 9:
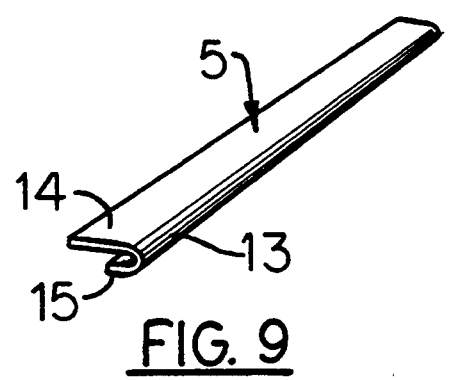
FIG. 9 is a perspective view of a side guard protection device for treating ingrown toenails and utilized in the method shown in FIGS. 1-8.

FIG. 9 shows the details of the side guard protector 5. The side guard protector 5 comprises a flattened U-shaped channel member, with one arm 14 of the U-shaped member being generally wider than the other arm 15, with both arms being joined at a middle section 13. The material itself is made from a relatively thin, but rigid plastic material. The narrow arm 15 is long enough to lip under the underside of the nail 2, and the wide arm 14 of the guard 5 provides a surface for the adhesive to affix the guard 5 to the top surface of the nail 2. The inner surface of the middle section 13 of the guard 5 is formed as either an angled V-shape, or a square box shape, or a rounded U-shape with a dimension or radius between the first arm 14 and second arm 15 which is sufficiently small to fit snugly around the edge 4 of the nail 2.

As the nail 2 grows, the guard 5 will advance with the nail growth. The guard 5 will insist that the nail 2 grow straight forward rather than in an ingrown pattern. The application of the guard 5 should be inspected periodically to ensure secure adherence to the nail 2, making adjustments as needed if the guard 5 has in any manner disengaged from the nail plate 2. In any event, the guard 5 should be maintained weekly to ensure continuing attachment to the nail plate 2. The guard 5 can be resecured by applying an adhesive 11 to the nail plate 2, spreading it evenly with an orangewood stick, keeping the adhesive away from the cuticle area, activating the adhesive 11 with the catalyst 7 and buffing the nail 2 smooth. Again, during each treatment, the nail free end should be filed 9 and shaped straight across to maintain a square shape. Maintenance may be repeated until the guard 5 is completely grown off the nail 2. If desired, the guard 5 may be removed by soaking the nail completely with an acetone polish remover until dissolved.

The adhesive 11 utilized in the treatment described above may comprise any thick or thin viscosity instant glue, crazy glue, adhesive, resin, or gel. The accelerator or catalyst 7 described above may comprise any nail glue drying accelerator, activator, kicker, adhesive speed dryer, or other suitable catalyst.

The side guard protector 5 and the method of treating ingrown toenails described above may be used on virtually any ingrown nail regardless of the size and shape of the particular person's toe or finger. A nail guard 5 which has been properly applied aesthetically appears like a normal nail, and the surface is smooth and straight, so that socks and stockings can be worn without catching material on any sharp edges or corners.

Specific details of the invention disclosed above are not to be interpreted as limiting, but merely as a base for the claims and for teaching one skilled in the art to variously practice and construct the present invention in any appropriately detailed manner. Changes may be made in details of construction or practice of the invention without departing from the spirit of the invention, especially as defined in the following claims.

I claim:

1. A method for treating ingrown nails comprising:
   a) trimming the ingrown portion of the nail;
   b) providing a nail side guard;
   c) applying an adhesive to a side edge of the nail or to an inside cavity of the nail side guard;
   d) sliding the nail side guard under the side edge of the nail, beginning at a free end of the nail and continuing toward a base of the nail;
   e) spraying a catalyst onto the side edge of the nail for instantly adhering the nail side guard thereon;
   f) trimming any excess portion of the nail side guard;
   g) filing the free end of the nail square and straight;
   h) applying adhesive evenly across the entire top surface of the nail level with a thickness of the side guard;
   i) spraying the catalyst onto the evenly applied adhesive for instantly solidifying the adhesive on the top surface of the nail; and,
   j) buffing the nail smooth.

2. The method according to claim 1, further comprising providing a nail side guard which comprises a flattened U-shaped channel member, with a first arm of the member being relatively wide and lying on an upper surface near the side edge of the nail, and a second arm being relatively narrow and being lipped under an underside of the nail, with the first arm and second arm being joined at a middle section having an inner dimension sufficiently small to fit snugly around the side edge of the nail.

3. The method according to claim 2 further comprising repeating steps a) through g) to apply a second nail side guard to a second ingrown portion of the nail.

4. A side guard protection device for treating ingrown nails comprising, in combination:
   a flattened U-shaped channel member, said channel member extending longer than a length of an ingrown side edge of the nail and being made of a rigid plastic material instantly bondable to the nail with an adhesive and catalyst, and the plastic material being severable with a nail clippers, and said channel member further comprising a first arm which is relatively wide and conforms to an upper surface of the nail and a second arm which is relatively narrow for lipping under an underside edge of the nail, with the first and second arm being joined at a middle section having an inner dimension sufficiently small to fit snugly around a side edge of the nail, the channel member and narrow second arm thereof thereby being slidable down under the side edge of the nail;

an adhesive for bonding the relatively wide first arm to the upper surface of the nail and for applying a leveling surface across the upper surface of the nail level with a thickness of the first arm of the channel member; and, a catalyst for instantly drying said adhesive;

whereby said channel member becomes bonded to and advances the growth of said nail for the purpose of straightening the growth of said nail.

* * * * *